United States Patent [19]

Jones et al.

[11] 4,225,730

[45] Sep. 30, 1980

[54] PROCESS FOR PREPARING 4-(2,4-DIFLUOROPHENYL)-SALICYCLIC ACID

[75] Inventors: Howard Jones, Holmdel, N.J.; Robert W. Houser, Wapakoneta, Ohio

[73] Assignee: Merck & Co., Inc., Rahway, N.J.

[21] Appl. No.: 905,086

[22] Filed: May 11, 1978

Related U.S. Application Data

[63] Continuation of Ser. No. 567,201, Apr. 16, 1975, abandoned, and a continuation-in-part of Ser. No. 490,620, Jul. 22, 1974, abandoned.

[51] Int. Cl.$^2$ ............................................. C07C 69/76
[52] U.S. Cl. ............................... 562/469; 260/649 F; 560/130; 568/319; 568/331
[58] Field of Search ........................................ 562/469

[56] References Cited

U.S. PATENT DOCUMENTS 3,681,445  8/1972  Ruyle .................................. 562/469

Primary Examiner—Paul J. Killos
Attorney, Agent, or Firm—Raymond M. Speer; William H. Nicholson

[57] ABSTRACT

5-(2,4-difluorophenyl)salicylic acid, an anti-inflammatory, anti-pyretic, analgesic agent is prepared by: (1) diazotizing 2,4-difluoroaniline in the presence of benzene to yield 2,4-difluorobiphenyl; (2) Friedel-Crafts acylation to produce 2',4'-difluoro-4-alkanoylbiphenyl; (3) oxidation of the alkanoyl group to produce 2',4'-difluoro-4-alkanoyloxybiphenyl; (4) hydrolysis of the alkanoyl group to produce 4-(2,4-difluorophenyl)-phenol; and (5) Kolbe-Schmitt carboxylation to produce the final product.

8 Claims, No Drawings

PROCESS FOR PREPARING 4-(2,4-DIFLUOROPHENYL)-SALICYCLIC ACID

This is a continuation of Ser. No. 567,201, filed Apr. 16, 1975, which was a continuation-in-part of Ser. No. 490,620, filed July 22, 1974, both now abandoned.

This invention relates to a process for the preparation of 5-(2,4-difluorophenyl)salicylic acid, and to the process for the preparation of the intermediate precursor thereto, 4-(2,4-difluorophenyl)phenol, and to certain novel intermediates in the process.

The final product of the novel process of this invention is useful as an anti-inflammatory, anti-pyretic and analgesic agent and is described in U.S. Pat. No. 3,714,226.

The novel process of this invention to the intermediate 4-(2,4-difluorophenyl)phenol and to 5-(2,4-difluorophenyl)salicylic acid, comprises four and five steps respectively and are described below in seriatim.

Step A

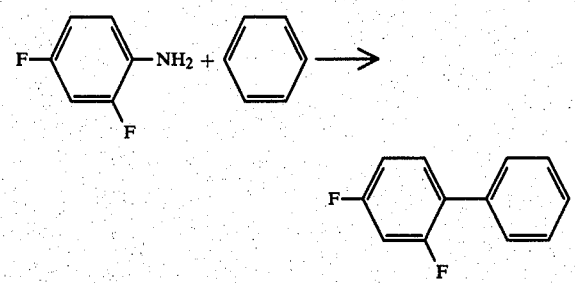

Approximately equimolar amounts of 2,4-difluoroaniline and a diazotizing reagent such as isoamyl nitrite, sodium nitrite, nitrogen trioxide or nitrogen trioxideboron trifluoride complex, preferably a slight excess of the latter, are added to an excess of benzene. The amount of benzene is not critical, and it is convenient to use sufficient of it to act as solvent for the reaction. The reaction, however, can be conducted in an inert solvent with close to the stoichiometric amount of benzene. The reaction is initiated by warming to 60°–70° C. when bubbling begins. The mixture is then maintained between ambient and reflux temperatures for 3–64 hours. It is preferred to conduct the reaction at reflux temperature for 3 to 8 hours.

Isolation of the product can be accomplished by any routine manipulation, such as evaporation of the excess solvents, steam distillation of the product, and crystallization.

Step B

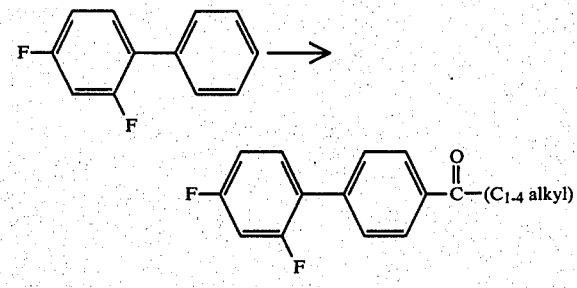

2,4-Difluorobiphenyl from Step A is acylated by a Friedel-Crafts reaction with $C_{2-5}$ alkanoic acid anhydride or $C_{2-5}$ alkanoic acid halide and a Friedel-Crafts catalyst such as aluminum chloride, boron trifluoride, ferric chloride or titanium tetrachloride in an inert organic solvent such as a chlorinated hydrocarbon, for example methylene chloride, chloroform, 1,1,2,2-tetrachloroethane, or carbon disulfide. The reaction is conducted at between about 10° C. and reflux temperature, preferably at 10°–25° C. for 2 to 4 hours. The product is isolated in the usual way by decomposing excess Friedel-Crafts catalyst and evaporation of solvents.

Step C

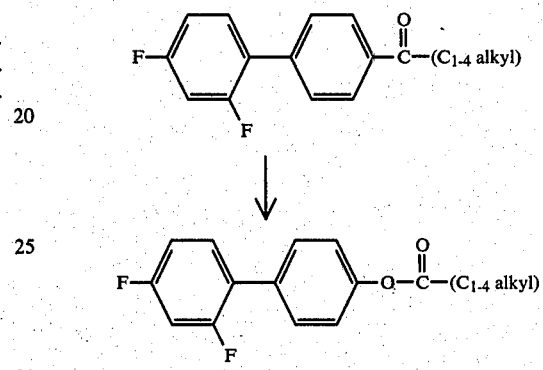

The product from Step B is treated with an excess of an oxidizing agent such as pertrifluoroacetic acid, m-chloroperbenzoic acid, perphthalic acid, permaleic acid, p-methoxycarbonylperbenzoic acid, peracetic acid, or the like in an inert organic solvent such as dimethylformamide or a chlorinated hydrocarbon, for example 1,2-dichloroethane, chloroform, methylene chloride, or the like or mixtures of a chlorinated hydrocarbon and a lower alkanoic acid such as acetic acid of up to about 25% alkanoic acid at 50° C. to reflux temperature for 4–12 hours. In some cases it is advantageous to prepare the peracid in situ by employing a mixture of the normal acid anhydride and an oxidizing agent such as hydrogen peroxide. The product is isolated from the cooled reaction mixture by conventional techniques such as evaporation of the solvent and recrystallization.

Step D

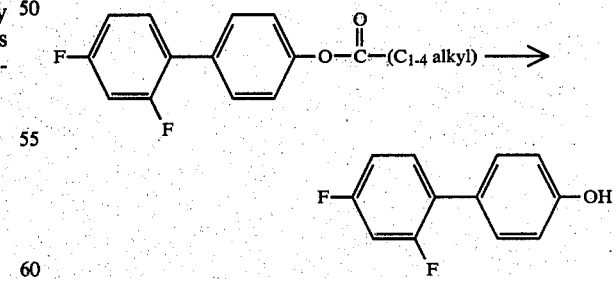

The ester product from Step C is hydrolyzed by standard acid hydrolysis or alkaline saponification, followed by acidification. In either case, the product crystallizes from the aqueous acid solution and is collected on a filter.

The alkaline saponification is conveniently performed with 50% (w/v) aqueous sodium hydroxide or potassium hydroxide at reflux temperature for 2-4 hours. The hot aqueous solution is then acidified and cooled.

The acid hydrolysis is conveniently conducted by warming at 50° C. to reflux temperature in aqueous or alkanolic 3-6 N mineral acid such as hydrochloric or sulfuric acid for 3-6 hours followed by cooling.

Step E

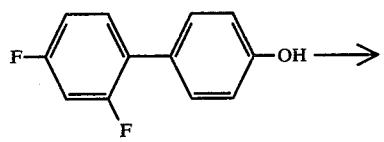

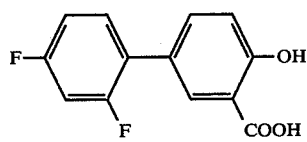

The 4-(2,4-difluorophenyl)phenol is carboxylated under Kolbe-Schmitt conditions at 200°-260° C. and 1100 to 1400 p.s.i. of carbon dioxide for 4-8 hours, in the presence of an alkali metal carbonate, preferably, potassium carbonate. Operationally, the reaction pressure vessel is conveniently pressurized at ambient temperature to 800-1000 p.s.i. with carbon dioxide and then heated to reaction temperature. The cooled reaction mixture is dissolved in water and acidified to pH 2 or less and the precipitated product is collected.

Alternatively, the ester product from Step C can be saponified with alkali, the reaction mixture cooled to crystallize the alkali metal salt which is then filtered off. The dry alkali metal salt is carboxylated in an autoclave at 200°-260° in an atmosphere of $CO_2$ at a pressure of 1100-1400 p.s.i. The cooled reaction mixture is dissolved in water and acidified to pH 2 or less and the precipitated product collected.

The above-described process, although involving five steps, has a distinct advantage over prior art processes for the preparation of 5-(2,4-difluorophenyl)salicylic acid. The known process involves fewer steps, being as follows:

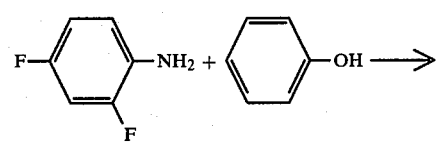

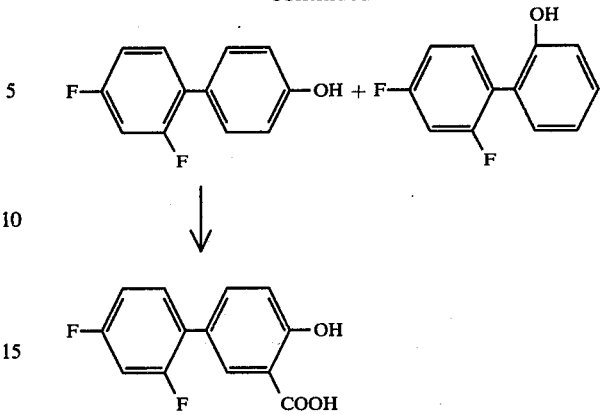

However, as indicated, the diazo coupling reaction produces a mixture of isomers with the concomitant reduction in yield. More importantly, the isomers are so difficultly separated that the process is not commercially feasible compared with the novel sequence of steps of the present invention.

Another important advantage of the novel process of this invention is that acylation is the only substitutive reaction with biphenyl that yields practically exclusively a para- isomer and is easily convertible to a 4-phenylphenol.

Other embodiments of this invention are the sequences of Steps B through E, C through E, A through D, B through D, and C to D.

Another embodiment of this invention is the novel intermediates produced by the novel process, namely 2,4-difluorobiphenyl, 2,4-difluoro-4'-($C_{2-5}$ alkanoyl)-biphenyl, and 2,4-difluoro-4'-($C_{2-5}$ alkanoyloxy)biphenyl.

The following example describes the process in detail. It is not intended that the invention be limited to the particular pressures, temperatures, times, and reagents recited in the following examples, but rather that they be exemplary only.

EXAMPLE 5-(2,4-Difluorophenyl)salicylic Acid

Step A: Preparation of 2,4-difluorobiphenyl

To a 50 liter resin pot equipped with stirrer, thermometer, nitrogen-inlet, internal steam coil and reflux condenser is charged 31.5 liters of benzene, 1.025 liters of isoamyl nitrite and 700 g. (5.43 moles) of 2,4-difluoroaniline.

The reaction mixture is heated to reflux. Vigorous nitrogen evolution begins at 70° C. Reflux begins at 74° and rises to 77° during the reaction period. The batch is refluxed for 5 hours. The benzene is atmospherically distilled (required 3.5 hours) and the residue is steam distilled until a single-phase distillate is collected (required 10 hours). The layers are separated and the aqueous portion is extracted with 2×2.6 liters of benzene. The combined benzene extracts are washed with 2×2.6 liters of water, dried over anhydrous magnesium sulfate and filtered. This dried benzene layer is combined with that from an identical run and the benzene is removed in vacuo. The residue, crude 2,4-difluorobiphenyl, weighed 1.321 kg. This crude is dissolved in a mixture of 4.4 liters isopropanol and 2.2 liters of water at 65°. The solution is cooled slowly to 25°, seeding during the cooling period, and aged at 25° for one hour. The batch is cooled to 0°–5°, aged at 0°–5° for one hour, and the solids are filtered, washed with 3×360 ml. of cold (0°) isopropanol/water (2/1) and then slurry-washed with 3.6 liters of water. The cake is air dried. Yield, 1.092 kg. (52.5%), m.p. 61°–63°.

Step B: Preparation of 4-(2,4-difluorophenyl)acetophenone

Into a 12 liter r.b. flask, fitted with stirrer, thermometer, reflux condenser, addition funnel and nitrogen-inlet is charged 1.27 kg. (9.55 moles) of anhydrous aluminum chloride to 3.1 liters of methylene chloride. To this mixture is added 449 ml. (485 g.; 4.75 moles) of acetic anhydride at 15°–20° over a 20 minute period. To the resulting stirred solution is added 745 g. (3.92 moles) of 2,4-difluorobiphenyl in 1.88 liters of methylene chloride at 20°–25° over 45 minutes. The reaction is complete after 2.5 hours at 25° and the batch is quenched into 18.8 liters of ice and water. The layers are separated and the aqueous portion extracted with 2×6.2 liters of methylene chloride. The combined methylene chloride layers are washed with 3.4 liters of water, 6.2 liters of 20% aqueous sodium carbonate solution and 3.4 liters of water. After drying over anhydrous magnesium sulfate and filtering, the methylene chloride is removed in vacuo. Yield, 895.5 g. (98.5%); m.p. 78°–79°.

Step C: Preparation of 4-(2,4-difluorophenyl)phenylacetate

A 1.0 liter, three-necked round-bottom flask was fitted with stirrer, thermometer, reflux condenser and addition funnel. Fifty grams (50 g.; 0.216 mole) of 4-(2',4'-difluorophenyl)acetophenone, 92.2 g. (0.94 moles) of maleic anhydride, 198 ml. of methylene chloride and 48.7 ml. of glacial acetic acid were charged to the flask and heated to reflux (52°). A cold 50% aqueous hydrogen peroxide solution (22.2 g.; 0.326 moles as peroxide) was added, dropwise, over 30 minutes at reflux temperature. The batch was refluxed for an additional 7 hours, then cooled to 25°.

Solid sodium bisulfite (24.0 g.; 0.231 mole) was added to the batch, followed by 4.5 ml. of water. After stirring for 15 minutes at 25°, anhydrous sodium sulfate (7.5 g.) was added and the batch stirred for two hours at 25°. The solids were filtered and washed with 4×35 ml. of methylene chloride. The combined filtrate and washes were concentrated in vacuo to dryness, flushed once with 75 ml. of isopropanol and again taken to dryness in vacuo (75 g.). This crude was recrystallized from 105 ml. of hot (80° C.) isopropanol. The clear solution was cooled to 0° and aged at 0° for 2 hours. The product was filtered, washed twice with mother liquors, then with 3×10 ml. of cold (0° C.) isopropanol and dried in vacuo at 50°. Yield, 48.7 g. (91%); m.p. 104°–107° C.

Step D: Preparation of 4-(2,4-difluorophenyl)phenol

A 30 liter resin pot is fitted with stirrer, thermometer and reflux condenser, and charged with 2.62 kg. of 50% aqueous sodium hydroxide and 11.34 liters of water. 4-(2',4'-Difluorophenyl)phenylacetate (1.876 kg., 7.55 m) is added and the batch is heated to reflux over 2.5 hours. The batch is refluxed for 2 hours (in solution at 75°), then cooled to 100° and added to a solution of 3.27 liters of concentrated hydrochloric acid in 9.8 liters of water in a 50 liter resin pot over a 30 minute period.

The temperature of the acid mixture rises to 40° during the addition. The batch is cooled to 20°, filtered on a 20" pot (paper and cloth) and washed with 4×4.06 liters of water. The batch is air-dried at 80°. Yield, 1.512 kg. (97.5%); m.p. 152°–154°. K.F., 0.12%.

Step E: Preparation of 5-(2,4-difluorophenyl)salicylic Acid

Anhydrous potassium carbonate (7.2 kg.; 52.0 moles) and 1.402 kg. (6.8 moles) of 4-(2',4'-difluorophenyl)phenol are blended in a Fitzmill and charged to a 5 gal. autoclave which is previously pressure-tested to 1900 p.s.i. with nitrogen. The autoclave is pressurized to 890 p.s.i. with $CO_2$ and the agitator is started. The batch is heated to 240° (2.25 hours heat-up time) and aged at 236°–246° for 6 hours. The reaction mixture is allowed to cool overnight and the autoclave is carefully vented. The solids are removed (weight of solids, 8.855 kg.) and transferred to a 20–30 gal. portable extractor. Add 5.5 gal. of water, agitate 15 minutes at 20°–25° and filter on a 19" pot set with cloth, paper and cloth. The cake is sucked to damp-dry and charged to a 100 gal. still with 37 gal. of water. The batch is heated to 80° (steam) and then 69.5 g. of tetrasodium versenate and 116 g. of Nuchar C-190N are added. Continue heating to 90° and filter through a Sparkler set with cloth, paper and cloth and pre-coated with Supercel. The Sparkler is washed with 3×4 gal. of 60°–70° water. The filtrate and washes are recharged to the clean still and the batch is acidified with 550 ml. of concentrated sulfuric acid (pH 2). The slurry is aged for 10 minutes and cooled to 25°. The solids are filtered on a 19" pot (cloth, paper, cloth), washed with 4×2 liters of water and dried in vacuo at 70° until K.F. 1.0%. Yield, 1.507 kg. (88.5%, crude); m.p. 210°–212°.

A 50 liter resin pot is fitted with stirrer, thermometer, and steam coil and charged with 728.5 g. of crude 5-(2,4-difluorophenyl)salicylic acid. Toluene (34 liters) is added and the batch is heated to effect solution (104°–108°). The batch is filtered through an 8" Sparkler filter.

A second, identical batch is processed in the same manner through the Sparkler filter and the Sparkler is washed with 5 gal. of hot toluene.

The combined filtrates are refrigerated over the weekend and filtered on a 20" pot set with cloth and paper. The solids are washed with one gallon of cold toluene and sucked damp-dry on the pot. The cake is trayed and air dried to constant weight at 75°. The drying process is finished in vacuo at 75°–80°. Yield, 1.352 kg. (93% recovery); m.p. 212°–213°.

What is claimed is:

1. A process for the preparation of a compound of formula:

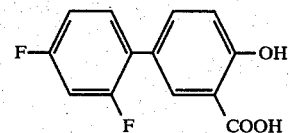

which comprises in sequence, the following steps:
(a) diazotizing 2,4-difluoroaniline in the presence of benzene to produce 2,4-difluorobiphenyl;
(b) acylating the product of Step (a) in the presence of a Friedel-Crafts catalyst with a $C_{2-5}$ alkanoic acid anhydride or $C_{2-5}$ alkanoic acid halide to produce 4-($C_{2-5}$ alkanoyl)-2',4'-difluorobiphenyl;
(c) oxidizing the $C_{2-5}$ alkanoyl group of the product of Step (b) to produce 4-($C_{2-5}$ alkanoyloxy)-2',4'-difluorobiphenyl;

(d) hydrolyzing the C$_{2-5}$ alkanoyl group from the product of Step (c) to produce 4-(2,4-difluorophenyl)phenol or alkali metal salt thereof;

(e) carboxylating the product of Step (d) to produce the product 5-(2,4-difluorophenyl)salicylic acid.

2. The process of claim 1, wherein
   (a) the diazotization is conducted with isoamyl nitrite at 60° C. to reflux temperature;
   (b) the Friedel-Crafts catalyst is aluminum chloride and the acylation is conducted at 10°-25° C.;
   (c) the oxidation is conducted with permaleic acid at 50° C. to reflux temperature;
   (d) the hydrolysis is conducted at 50° C. to reflux temperature with aqueous alkali metal hydroxide or aqueous or alkanolic mineral acid; and
   (e) the carboxylation of the phenol or its alkali metal salt is conducted at 1100-1400 p.s.i. and 200°-260° C. with carbon dioxide and in the case of the phenol, in the presence of an alkali metal carbonate.

3. A process for the preparation of a compound of formula:

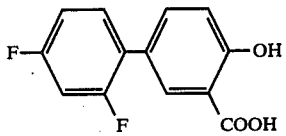

which comprises in sequence the steps of:
   (a) acylating 2,4-difluorobiphenyl with a C$_{2-5}$ alkanoic acid anhydride or C$_{2-5}$ alkanoic acid halide in the presence of a Friedel-Crafts catalyst to produce 4-(C$_{2-5}$ alkanoyl)-2',4'-difluorobiphenyl;
   (b) oxidizing the product of Step (a) to produce 4-(C$_{2-5}$ alkanoyloxy)-2',4'-difluorobiphenyl;
   (c) hydrolyzing the C$_{2-5}$ alkanoyl group from the product of Step (b) to produce 4-(2,4-difluorophenyl)phenol or alkali metal salt thereof;
   (d) carboxylating the product of Step (c).

4. The process of claim 3, wherein
   (a) the Friedel-Crafts catalyst is aluminum chloride and the acylation is conducted at 10°-25° C.;
   (b) the oxidation is conducted with permaleic acid at 50° C. to reflux temperature;
   (c) the hydrolysis is conducted at 50° C. to reflux temperature with aqueous alkali metal hydroxide or aqueous or alkanolic mineral acid; and
   (d) the carboxylation of the phenol or its alkali metal salt is conducted at 1100-1400 p.s.i. and 200°-260° C. with carbon dioxide and in the case of the phenol, in the presence of an alkali metal carbonate.

5. A process for the preparation of a compound of formula:

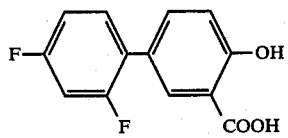

which comprises in sequence the steps of:

(a) oxidizing a compound of formula:

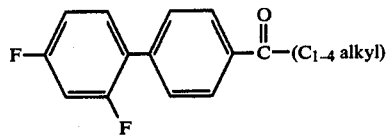

to produce the compound of formula:

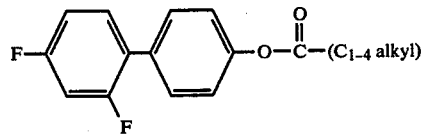

(b) hydrolyzing the product of Step (a) to produce 4-(2,4-difluorophenyl)phenol or alkali metal salt thereof;
(c) carboxylating the product of Step (b).

6. The process of claim 5, wherein
   (a) the oxidation is conducted with permaleic acid at 50° C. to reflux temperature;
   (b) the hydrolysis is conducted at 50° C. to reflux temperature with aqueous alkali metal hydroxide or aqueous or alkanolic mineral acid; and
   (c) the carboxylation of the phenol or its alkali metal salt is conducted at 1100-1400 p.s.i. and 200°-260° C. with carbon dioxide and in the case of the phenol, in the presence of an alkali metal carbonate.

7. A process for the preparation of a compound of formula:

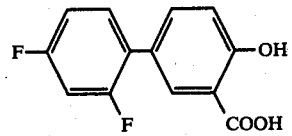

which comprises in sequence the steps of:
   (a) hydrolyzing a compound of formula:

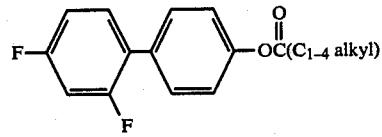

to produce 4-(2,4-difluorophenyl)phenol or alkali metal salt thereof; and
   (b) carboxylating the product of Step (a).

8. The process of claim 7, wherein
   (a) the hydrolysis is conducted at 50° C. to reflux temperature with aqueous alkali metal hydroxide or aqueous or alkanolic mineral acid; and
   (b) the carboxylation of the phenol or its alkali metal salt is conducted at 1100-1400 p.s.i. and 200°-260° C. with carbon dioxide and in the case of the phenol, in the presence of an alkali metal carbonate.

* * * * *